United States Patent [19]

Geissler et al.

[11] 4,056,101

[45] Nov. 1, 1977

[54] MEANS FOR REDUCING TISSUE THROMBOPLASTIN IN COLLECTED BLOOD

[75] Inventors: Ulrich C. Geissler, Cary; William J. Stith, Mundelein, both of Ill.

[73] Assignee: Baxter Travenol Laboratories, Inc., Deerfield, Ill.

[21] Appl. No.: 719,556

[22] Filed: Sept. 1, 1976

[51] Int. Cl.² ............................................. A61M 5/00
[52] U.S. Cl. ............................... 128/214 D; 128/2 G; 128/272; 128/275; 128/DIG. 24; 128/DIG. 5
[58] Field of Search ............... 128/275, 276, 272, 274, 128/214 R, 214 D, 214.2, DIG. 24, DIG. 5, 2 F, 2 G

[56] References Cited

U.S. PATENT DOCUMENTS

| 2,950,716 | 8/1960 | Bellamy, Jr. et al. | 128/214 D |
| 3,467,095 | 9/1969 | Ross | 128/214.2 |
| 3,654,924 | 4/1972 | Willson et al. | 128/214 D |

Primary Examiner—John D. Yasko
Assistant Examiner—Henry S. Layton
Attorney, Agent, or Firm—Henry W. Collins; George H. Gerstman; Paul C. Flattery

[57] ABSTRACT

A closed blood collection system is provided which reduces the amount of tissue thromboplastin that is mixed with the collected blood. The system includes a secondary blood receptacle for collecting an initial volume of blood, up to 5 ml, prior to collection of the remainder of the blood in a main container with anticoagulant. Means are provided for directing the initial volume of blood into the secondary blood receptacle and for directing the blood subsequently collected into the main blood container.

4 Claims, 3 Drawing Figures

MEANS FOR REDUCING TISSUE THROMBOPLASTIN IN COLLECTED BLOOD

BACKGROUND OF THE INVENTION

The present invention relates to collection of blood for use in blood transfusions.

In the collection of blood, when the needle is inserted into the skin, and particularly when the needle is moved around to find the vein, there is generally some tissue trauma. Normally the tissue trauma that results from cutting or opening the skin causes the release of an amount of tissue thromboplastin to aid in the proper clotting of the blood.

However, it has been found that blood collected for use in blood transfusions should be free of tissue thromboplastin, even in low levels, because any tissue thromboplastin that is present will cause activation of the fibrinolytic system. Such activation can in turn result in decreased levels of antihemophilic factor (AHF) and platelets. AHF and platelets are components prepared from fresh blood and find uses in the treatment of hemophilia A and cancer, respectively. These disease conditions require treatment with relatively large amounts of the respective blood components.

It is, therefore, an object of the present invention to provide a device and method for reducing tissue thromboplastin in collected blood.

Another object of the present invention is to provide an efficient device for removing the initial volume of blood collected, which initial volume is expected to have the greatest possibility of tissue fluid contamination.

Another object of the present invention is to provide a system that is simple in construction and easy to use which aids in maximizing the levels of available AHF and platelets in collected blood, by preventing an initial volume of collected blood from entering the main blood container.

Other objects and advantages of the invention will become apparent as the description proceeds.

SUMMARY OF THE INVENTION

In accordance with the present invention, a method is provided for reducing the amount of tissue thromboplastin that is present in the collected blood. The method comprises the steps of attaching a phlebotomy needle to a donor, collecting an initial volume of blood (up to 5 ml) in a blood receptacle, and thereafter collecting the blood after the initial volume in a main blood container.

In the illustrative embodiment, a blood collection system is provided which includes a phlebotomy needle, a main blood container, and tubing for coupling the needle to the main container. The improvement comprises a secondary blood container for collecting an initial volume of blood prior to collection of the blood in the main blood container. Means couple the secondary blood container to the tubing. Means are also provided for preventing the initial volume of blood from flowing into the main blood container and for channeling flow of the blood, after collection of the initial volume, into the main blood container.

In the illustrative embodiment, the secondary blood container comprises a blood receptacle concentrically positioned about the tubing. A valve connected to the tubing within the receptacle is open during initial blood flow and causes the initial flow to be collected in the receptacle. The valve is subsequently closed and the remaining blood flow is collected in the main blood container.

A more detailed explanation of the invention is provided in the following description and claims, and is illustrated in the accompanying drawings.

DETAILED DESCRIPTION OF THE ILLUSTRATIVE EMBODIMENT

Figure 2:
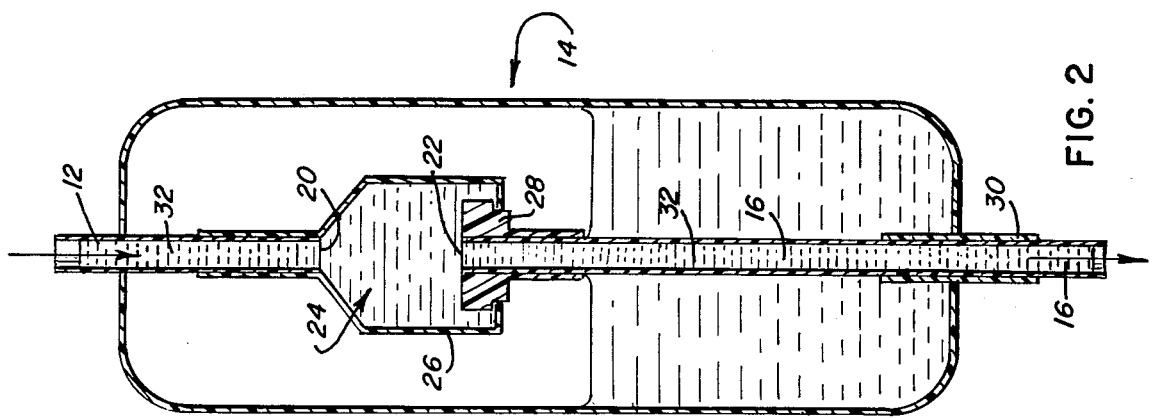
FIG. 2 is an assembly view thereof, in schematic form, showing the blood flow valve in its closed position.
Figure 3:
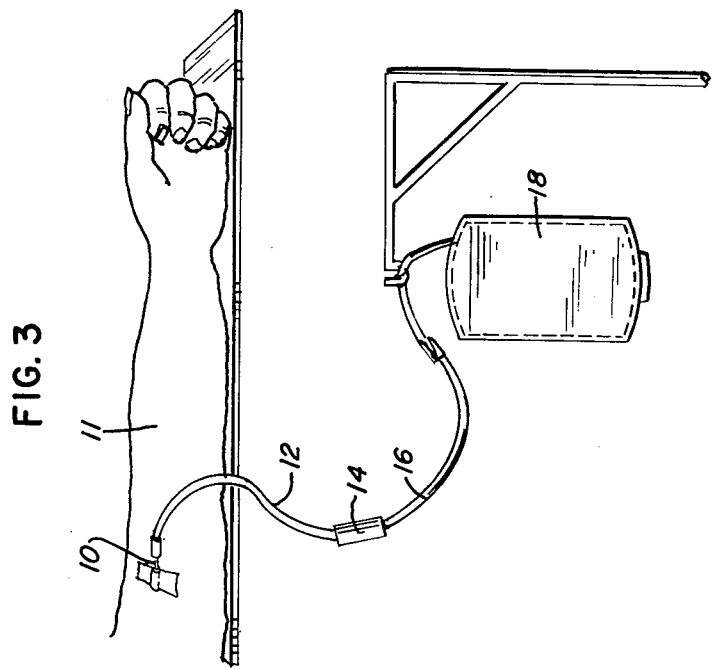
FIG. 3 is a view of a blood collection system which employs the secondary blood receptacle of FIGS. 1 and 2.

Referring to the drawings, the blood collection system shown therein comprises a conventional phlebotomy needle 10 for insertion into the vein of a donor 11. Needle 10 is coupled via inlet tubing 12 to an initial blood receptacle 14. Also coupled to initial blood receptacle 14 is outlet tubing 16 which is connected to a main blood container or blood bag 18. Inlet tubing 12 and outlet tubing 16 is preferably conventional blood tubing having an internal diameter of less than ⅛ inch.

In the illustrative embodiment, receptacle 14 is positioned concentrically about open end 20 of tube 12 and open end 22 of tube 16. A valve 24 is utilized to couple ends 20 and 22 in the manner about to be described.

Figure 1:
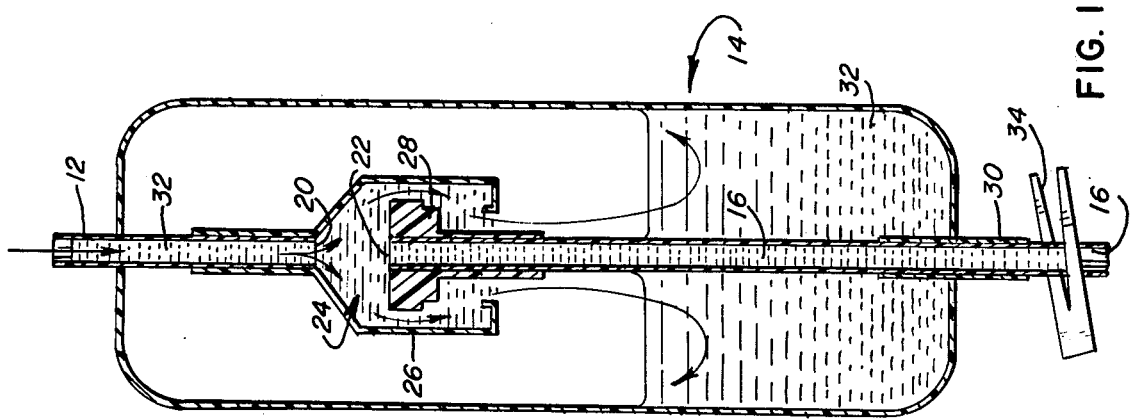
FIG. 1 is an assembly view, in schematic form, of a secondary blood receptacle constructed in accordance with the principles of the present invention, with the blood valve in its open position.

A valve stem 28 is connected adjacent tube end 22 and valve seat 26 is connected adjacent tube end 20. Tube 16 is slidable with respect to a sleeve 30 fastened to the bottom of receptacle 14. Valve 24 is normally in the position illustrated in FIG. 1, with valve stem 28 separated from valve seat 26. In this manner, during initial flow of blood 32 from the donor, with tube 16 closed off by clamp 34, the blood will flow via tube 12 into receptacle 14. Since open end 22 is small (preferably less than ⅛ inch internal diameter) when clamp 34 is operative it is unlikely that any blood will enter tube 16 via open end 22.

After a predetermined amount of initial flow has occurred, tube 16 may be pulled downwardly (with respect to fixed sleeve 30) whereby valve stem 28 will engage valve seat 26, as shown in FIG. 2. Clamp 34 is then disengaged. In this manner, the remaining blood will flow via tube 12 and tube 16 into the blood bag 18.

It is preferred that the initial volume of blood separated from the main blood container 18 be less than or equal to 5 ml. It is believed that this initial volume contains the major amount of tissue thromboplastin. By separating this initial volume (and with it the tissue thromboplastin) and collecting the remainder in blood bag 18, the likelihood of clotting of the main body of blood is reduced and the available amount of available coagulation factors (principally AHF) and platelets is enhanced.

Although an illustrative embodiment of the invention has been shown and described, it is to be understood that various modifications and substitutions may be made by those skilled in the art without departing from the novel spirit and scope of the present invention.

What is claimed is:

1. In a blood collection system including a phlebotomy needle, a main blood container and tubing for coupling the needle to the main container, the improvement comprising: a secondary blood container for collecting an initial volume of blood prior to collection of the blood in the main blood container, said secondary blood container comprising a blood receptacle concentrically positioned about said tubing, said tubing being open within said receptacle during flow of said initial volume whereby said initial volume will flow to said receptacle; and means for collecting said initial volume in said secondary container and thereafter channeling flow of the blood into said main blood container.

2. A blood collection system as described in claim 1, said collecting and channeling means comprising a valve for maintaining said tubing open within said receptacle during the initial volume flow and for closing said tubing thereafter.

3. A blood collection system as described in claim 2, wherein said tubing comprises a pair of tubes each having an end located within said blood receptacle, and said valve includes a valve stem connected adjacent an end of one tube and a valve seat connected adjacent an end of the other tube.

4. A blood collection system as described in claim 3, including means movably connecting said tubing to said receptacle whereby movement of said tubing will control the opening and closing of said valve.

* * * * *